United States Patent [19]

Denney

[11] Patent Number: 5,057,435

[45] Date of Patent: Oct. 15, 1991

[54] REAGENT AND METHODS FOR CALCIUM DETERMINATION

[75] Inventor: Jerry W. Denney, Lachine, Canada

[73] Assignee: Synermed, Inc., Quebec, Canada

[21] Appl. No.: 597,181

[22] Filed: Oct. 12, 1990

[51] Int. Cl.$^5$ .................. G01N 21/25; G01N 21/64
[52] U.S. Cl. ............................ 436/79; 436/74; 436/164; 436/166
[58] Field of Search .................. 436/74, 79, 166, 164

[56] References Cited

U.S. PATENT DOCUMENTS

| | | | |
|---|---|---|---|
| 3,798,000 | 3/1974 | Helger | 23/230 B |
| 3,822,116 | 7/1974 | Morin | 23/230 B |
| 3,934,977 | 1/1976 | Cleaver | 23/230 B |
| 3,938,954 | 2/1976 | Stavropoulos et al. | 23/230 B |
| 4,382,122 | 5/1983 | Mezei et al. | 436/74 |
| 4,448,889 | 5/1984 | Neri et al. | 436/74 |

FOREIGN PATENT DOCUMENTS 0067041 12/1982 European Pat. Off. .
1137541A 1/1988 European Pat. Off. .
2335350 10/1974 Fed. Rep. of Germany .

OTHER PUBLICATIONS

Baginski et al., "Direct Microdetermination of Serum Calcium", Clin. Chim. Acta, 46, 49–54, 1973, p. 50.

*Primary Examiner*—David L. Lacey
*Assistant Examiner*—David Redding
*Attorney, Agent, or Firm*—Baker & Daniels

[57] ABSTRACT

A single, stable reagent and automatable methods utilizing the reagent for the assay of calcium in serum and aqueous samples, such as urine. (Aqueous samples contain little or no protein.) The reagent includes arsenazo III, 8-hydroxyquinoline, a buffer that does not bind calcium competitively with arsenazo III and that provides a reagent pH from about 8.5 to about 10, the buffer being in sufficient amount to maintain pH within +/− 0.1 pH units of the reagent pH when the reagent is added to a sample of unknown calcium content, dimethylsulfoxide and water. Importantly, dimethylsulfoxide permits the incorporation of 8-hydroxyquinoline into a single, stable reagent, which is at an alkaline pH that is optimal for calcium measurement by the calcium-arsenazo III complex. 8-Hydroxyquinoline eliminates assay interference due to magnesium ion. Also, at least one non-ionic surfactant in sufficient amount to minimize lipid turbidity may be added to the reagent. Spectral measurements of calcium-arsenazo III are made at wavelengths that minimize interference from lipemia, hemolysis, and bilirubinemia. Spectral interference from lipemia and hemolysis is further reduced by employing bichromatic measurements of the calcium-arsenazo III complex and by employing serum blank measurements.

28 Claims, No Drawings

REAGENT AND METHODS FOR CALCIUM DETERMINATION

FIELD OF INVENTION

The invention relates to the assay of calcium ion in bodily fluids.

BACKGROUND OF THE INVENTION

Serum calcium exists in two major forms. About half of the calcium in serum circulates as free ions and the other half is bound to circulating proteins. The small amount of calcium in blood is regulated by the parathyroid gland and the serum total protein level. Calcium ions participate in blood coagulation, neuromuscular conduction, maintenance of membrane function, intracellular regulations of glandular secretion, and control of skeletal and cardiac muscle contractility.

Colorimetric methods for determining the calcium content of serum must differentiate between spectrophotometric absorbance of a calcium-chromogen complex, such as calcium-arsenazo III, and spectrophotometric interferences due to lipemia, bilirubinemia, and hemolysis. Further, under alkaline pH conditions magnesium ion competitively binds to the chromogen, thereby producing assay interference. 8-Hydroxyquinoline effectively binds magnesium ion, thereby removing it as an interferant in the calcium assay.

Calcium reagents that include 8-hydroxyquinoline are disclosed in Neri et al., U.S. Pat. No. 4,448,889, Mezei et al., U.S. Pat. No. 4,382,122, Gindler, U.S. Pat. No. 3,754,865, and Stavropoulos et al., U.S. Pat. No. 3,938,954. However, these references do not disclose a single reagent for calcium assay. Rather, two reagents are required for the determination of calcium in serum. One reagent is an acidic dye reagent which includes a chromogen, a surfactant, and 8-hydroxyquinoline. The other reagent is a buffer reagent that includes an alkaline buffer.

A single calcium reagent is disclosed by Cleaver, U.S. Pat. No. 3,934,977. However, the reagent disclosed by Cleaver includes an acidic buffer. Further, reagent blank measurements, utilized in the calcium assay method disclosed in Cleaver, produce a high spectrophotometric absorbance.

Morin, U.S. Pat. No. 3,822,116, also discloses a single reagent for calcium assay. The reagent disclosed by Morin does not include 8-hydroxyquinoline.

Helger, U.S. Pat. No. 3,798,000, discloses a single reagent for calcium assay. The reagent has an alkaline pH and includes either 8-hydroxyquinoline sulfate or 8-hydroxyquinoline.

Bates et al., European Patent Application No. 88113754.1, discloses a single reagent for calcium assay. The reagent includes arsenazo III, but utilizes n acidic buffer and does not include 8-hydroxyquinoline.

Baginski et al., "Direct Microdetermination of Serum Calcium," Clin. Chim. Acta. 46, 49–54 (1973), discloses a multiple reagent system for calcium determination (p. 50). One of the reagents includes 8-hydroxyquinoline, dimethylsulfoxide, and acid (concentrated hydrochloric acid) (p. 50).

SUMMARY OF THE INVENTION

The invention is a single, stable reagent and automatable methods utilizing the reagent for the assay of calcium in serum, heparinized plasma, and aqueous samples, such as urine. (Aqueous samples contain little or no protein.)

The reagent includes arsenazo III, 8-hydroxyquinoline, a buffer, dimethylsulfoxide and water. The buffer must provide a reagent pH from about 8.5 to about 10, more preferably from about 8.5 to about 9.5, most preferably from about 8.8 to about 9, and must be in sufficient amount to maintain pH within $+/-0.1$ pH units of the reagent pH when the reagent is added to a sample of unknown calcium content.

The importance of a single reagent is that it is simpler for the assay operator to use than multiple reagents, and the importance of a stable reagent is that it permits accurate assays to be repeatedly performed and reagent waste and expense to be minimized.

The important aspect of the novel reagent is the inclusion of dimethylsulfoxide, which permits the incorporation of poorly soluble 8-hydroxyquinoline into a single, stable reagent that is buffered at an alkaline pH, where spectrophotometric absorbance of the sensitive colored complex calcium-arsenazo III is maximum. The reagent is preferably buffered at a pH of about 9. At a pH of about 9, calcium-arsenazo III maximally absorbs light at wavelengths that minimize interference from lipemia, hemolysis, and bilirubinemia. 8-Hydroxyquinoline binds to magnesium, which at an alkaline pH competes with calcium for complexation with arsenazo III, and removes it as an interferant in the assay for calcium.

The automatable assay methods utilizing the novel reagent maximize signal (spectrophotometric absorbance due to the calcium-arsenazo III complex) to noise (interfering spectrophotometric absorbances) ratio by spectrophotometrically measuring the calcium-arsenazo III complex at a pH and wavelength where the complex maximally absorbs light and where spectrophotometric interferences from lipemia, bilirubinemia, and hemolysis are reduced. Such spectral interferences are further reduced by performing bichromatic absorbance measurements (absorbance measurements at two different wavelengths), and by performing serum blank measurements.

DETAILED DESCRIPTION OF THE INVENTION

The invention is a single, stable reagent and method utilizing the reagent for the assay of calcium in serum and in aqueous samples, such as urine. (Aqueous samples contain little or no protein.)

Calcium Reagent
The general requirements for the calcium reagent are provided immediately below.

| | Ingredient | Amount |
|---|---|---|
| 1. | arsenazo III [also known as 2,2'-(1,8-dihydroxy-3,6-disulfonaphthylene-2,7-bisazo) bisbenzenearsonic acid] | In sufficient amount to react with all calcium in a sample of unknown calcium content |
| 2. | 8-hydroxyquinoline | In sufficient amount to bind all magnesium in the sample of unknown calcium content |
| 3. | a buffer that provides a reagent pH from about 8.5 to about 10 | In sufficient amount to maintain pH within $+/-0.1$ pH units of the reagent pH when the reagent is added to a sample of unknown calcium content |

| Calcium Reagent |  |
|---|---|
| The general requirements for the calcium reagent are provided immediately below. | |
| Ingredient | Amount |
| 4. dimethylsulfoxide | In sufficient amount to solubilize the 8-hydroxyquinoline in the reagent |
| 5. water, as a solvent | |

Preferably, at least one non-ionic surfactant, such as a polyoxyethylene alcohol (polyethylene glycol fatty alcohol ethers; ethoxylated fatty alcohols; macrogol fatty alcohol ethers), is added to the reagent in sufficient amount to minimize lipid turbidity. More preferably, a first non-ionic surfactant, such as a polyoxyethylene alcohol, and a second non-ionic surfactant, such as octoxynol (octylphenoxy polyethoxyethanol; polyethylene glycol p-isooctylphenyl ether), are added to the reagent in a combined concentration sufficient to minimize lipid turbidity and to provide mutual solubility of the first and second non-ionic surfactants in the reagent. In the most preferred embodiment, the second non-ionic surfactant is TRITON X-100 (available from Sigma Chemical Company) because it is a good lipemia clarifier. (However, TRITON X-100 may form turbid solutions with temperature changes.) The first non-ionic surfactant in the most preferred embodiment is a BRIJ surfactant (polyoxyethylene ethers available from Sigma Chemical Company), which prevents TRITON X-100 turbidity and aids in clarifying lipid turbidity.

Total surfactant concentration should be sufficient to minimize lipid turbidity without increasing reagent viscosity sufficiently to make reagent dispensing from an automated instrument inaccurate and imprecise. Total surfactant concentration in the reagent should be from about 0.1% (by volume) to about 2% (by volume). Total surfactant concentrations above about 2% (by volume) increase reagent cost with little additional lipid clearing effect. Further, total surfactant concentrations above about 2% may cause surfactant "carryover" to subsequent assays, which may be adversely affected by surfactants, in automated instruments that automatically wash and reuse reaction vessels and/or cuvettes and that perform assays in a random fashion.

A preferred buffer is 2-amino-2-methyl-1,3-propandiol (AMPD) because it can provide a reagent pH in the range most desired (a pH from about 8.8 to about 9) for spectrophotometric measurement of the calcium-arsenazo III complex, and has strong buffering capacity in that pH range. A sufficient concentration of AMPD to provide a reagent pH from about 8.8 to about 9 is about 0.2 molar. This concentration of buffer is chosen as an economic concentration required to closely maintain this pH range. Lower concentrations may be used for greater economy but there may develop a significant disparity between the spectrophotometric absorbance vs. concentration line slopes of aqueous and protein-containing (e.g., serum) samples. Higher concentrations of buffer may be used but the cost of the reagent is increased with little or no additional benefit.

Other buffers that can provide a reagent pH from about 8.5 to about 10 may be used but should be used in sufficient amount to maintain pH within +/−0.1 pH units of the reagent pH when the reagent is added to a sample of unknown calcium content. Further, the buffer employed must not bind calcium competitively with arsenazo III. Buffers that can provide a reagent pH from about 8.5 to about 9.5 and that do not bind calcium competitively with arsenazo III are more preferred than such buffers that provide a reagent pH from about 9.5 to about 10. Examples of buffers that may be used are dimethylaminomethanol, ethanolamine, and aminopropanol.

All of the above-stated buffers require the addition of an acid, which also must not bind calcium competitively with arsenazo III, to achieve the desired reagent pH. Examples of acceptable acids are hydrochloric, sulfuric, and acetic. If "carryover" of chloride ion from hydrochloric acid is a concern, particularly in automated analyzers that automatically wash and reuse reaction vessels and/or cuvettes and that perform tests in a random fashion, then acetic acid or sulfuric acid may be used. Acids that should not be used (because of their capacity to bind to calcium ion) are citric, oxalic, edetic, and phosphoric.

Because calcium binds to arsenazo III in a ratio of 1:1, there must be at least as many moles of arsenazo III as calcium in a test sample (described below in the Calcium Assay section) for calcium assay. The upper normal limit of calcium in serum is about 12 milligram (mg) percent (%). However, in order to account for abnormally high calcium levels in samples of unknown calcium content, the amount of arsenazo III in the test sample should be the molar equivalent of at least about 15 mg % calcium. (Abnormal calcium levels as high as 15 mg % are frequently encountered.) Further, because most clinical chemists desire linearity to at least about 20 mg % calcium, the amount of arsenazo III in the test sample is preferably the molar equivalent of at least about 20 mg % calcium.

A specific calcium reagent may be prepared by performing the following steps:

Step 1 - to 800 milliliters (ml) deionized water, add 21 grams (g) AMPD, 80 mg arsenazo III, 2 ml BRIJ 35 (a 30% wt./vol. solution) (BRIJ 35 is polyoxyethylene 23 lauryl ether), 1.2 ml TRITON X-100, and stir until a uniform solution is obtained;

Step 2 - add 10 g of CHELEX 100 to the uniform solution of Step 1 and mix thoroughly for 30 minutes; (Available from Bio-Rad Laboratories, Richmond, Calif., CHELEX 100 is a cation exchange resin used to remove divalent calcium and magnesium contaminants.)

Step 3 - remove the CHELEX 100 by filtration and adjust the pH of the filtrate to about 9 by addition of concentrated hydrochloric acid;

Step 4 - dissolve ½ g of 8-hydroxyquinoline in 100 ml of dimethylsulfoxide and add the resulting solution to the pH 9 filtrate obtained from Step 3;

Step 5 - add deionized water to the result of Step 4 until a total volume of about 1 liter is obtained.

The important aspect of the novel reagent is that the inclusion of dimethylsulfoxide in the reagent permits 8-hydroxyquinoline to be incorporated into a single, stable reagent, which is buffered at an alkaline pH that is optimal for measurement of calcium (optimal sensitivity of the calcium-arsenazo III complex). Without the inclusion of dimethylsulfoxide, a single calcium reagent must be acidic, or a separate reagent containing 8-hydroxyquinoline must be prepared.

The importance of a single reagent is that it is simpler for the assay operator to use than multiple reagents. Further, a stable reagent permits accurate assays to be repeatedly performed and reagent waste to be minimized. The present novel reagent is stable for at least one year at room temperature.

Calcium Assay

Blood serum contains indigenous spectrophotometrically absorbing substances, such as hemoglobin, bilirubin, and lipemic substances. These interferants most strongly absorb light in the shorter (red) wavelengths of the visible spectrum. Choosing a chromogen that when complexed with calcium ion absorbs light in the longer (blue) wavelengths of the visible spectrum importantly avoids much of the spectral interference from these indigenous serum substances. Arsenazo III is such a chromogen and when complexed with calcium ion has two absorbance maxima in the blue region of the visible spectrum (one maximum at about 595 to 600 nm and another maximum at about 650 to 655 nm). Further, absorbance of the calcium-arsenazo III complex is most intense at a pH of about 9. However, under alkaline conditions, magnesium ion, which is also indigenous in serum, interferes with the determination of calcium by the calcium-arsenazo III complex because magnesium will compete with calcium for binding to arsenazo III. The below-stated assay methods and the above-stated reagents work in conjunction to maximize the signal (spectrophotometric absorbance due to calcium-arsenazo III) to noise (interfering spectrophotometric absorbance due to lipemia, bilirubinemia, hemolysis, and magnesium) ratio, thereby producing a sensitive and accurate spectrophotometric assay for calcium.

Another important feature of a calcium assay is its adaptability to automation. Although some automated analyzers can perform an assay that requires a reaction time longer than about 10 minutes, the overwhelming majority of commercially available automated analyzers (such as the Hitachi 704, 707, 717 and 747 analyzers, and the Olympus AU 5000) cannot perform an assay that requires a reaction time longer than about 10 minutes, and a reaction time of less than 10 minutes is greatly preferred (see Takano et al., U.S. Pat. No. 4,588,695, col. 3, lines 29-31). Assay methods utilizing the present inventive reagent are adaptable to automation and can be performed on automated analyzers that require reaction times of about 10 minutes or less.

The most basic calcium assay of the present invention may be performed by the following steps:

Step 1 - prepare a test sample (ts) by adding a sample of unknown calcium content (serum or aqueous sample) to calcium reagent (described above);

Step 2 - prepare a test blank (tb) by adding deionized water to calcium reagent;

Step 3 - prepare a test standard (t stand) by adding a calcium standard of known calcium concentration to calcium reagent;

Step 4 - spectrophotometrically measure absorbances (A) of the test sample, the test blank, and the test standard at a wavelength from about 600 nm to about 670 nm;

Step 5 - calculate the concentration of calcium in the test sample by the equation $$\frac{A_{ts} - A_{tb}}{A_{t\,stand} - A_{tb}} \times \text{concentration of calcium standard} = \text{known calcium concentration of calcium in the test sample.}$$

Specifically, the above-stated assay may be performed by using 20 microliters (μl) of serum sample, 20 μl of deionized water, and 20 μl of calcium standard along with 2 ml of the specific calcium reagent described above (a 1:100 (vol.:vol.) dilution of sample:reagent).

In general, any of the above-stated reagents may be used in a calcium assay, and spectrophotometric measurements may be made from about 600 nm to about 670 nm, but are preferably made from about 650 nm to about 660 nm because interference due to lipemia is minimized at this wavelength range.

The calcium standard is preferably a reference serum with a known calcium concentration. The calcium concentration should be about that of normal serum. The upper concentration limit of calcium in normal serum is about 12 mg %, and a reference serum of 15 mg % calcium provides a suitable calcium standard. Protein in human serum may cause slight shifts in pH even when buffers at about 0.2 molar concentration are used, but the variation of protein from one patient sample to another will not cause significant variation in pH. Further, laboratories performing automated clinical analyses usually employ protein-based reference sera to calibrate a variety of assays because of the efficiency of using only one standard. If an aqueous standard is used as a calcium standard, a slight difference in the slope of the graph of absorbance versus concentration may exist between serum samples and the aqueous standard.

Spectral interference found in turbid or hemolytic serum samples, heparinized plasma samples, and turbid urine samples may be reduced by employing a serum blank (sb) in the assay. When a serum blank is employed in the assay described above, the test sample of Step 1 is prepared by adding a first portion of a serum sample (a sample of unknown calcium content) to the calcium reagent. In a separate step (Step 1A), a serum blank is prepared by adding a second portion of the serum sample (same volume as the first portion) to saline (same volume as the calcium reagent in Step 1). Steps 2 and 3 are performed as described above. Next (Step 3B), a test standard blank (t stand b) is prepared by adding calcium standard (same volume as the calcium standard in Step 3) to saline (same volume as calcium reagent in Step 1). In Step 4, the absorbance of the serum blank and test standard blank are spectrophotometrically measured (at a wavelength within the above-stated wavelength range) along with the absorbances of the test sample, test blank and test standard. Then in Step 5, the calcium concentration of the test sample is calculated by the equation $$\frac{A_{ts} - (A_{tb} + A_{sb})}{A_{t\,stand} - (A_{tb} + A_{t\,stand\,b})} \times \text{concentration of calcium standard} = \text{known calcium concentration of calcium in the test sample.}$$

Another means of reducing indigenous spectral interferences is by employing bichromatic measurements. Bichromatic measurements are performed by first measuring absorbances of the test sample, test blank, and test standard at a primary wavelength (1°λ), then measuring absorbances of the test sample, test blank, and test standard at a secondary wavelength (2°λ). The primary wavelength may be from about 640 nm to about 660 nm, and the secondary wavelength may be from about 700 nm to about 800 nm. This procedure further reduces spectral interference from turbidity because spectral absorbance due to calcium-arsenazo III decreases rapidly from the primary wavelength to the secondary wavelength, while absorbance due to turbidity remains relatively constant from the primary to the secondary wavelength. The concentration of calcium in the test sample may then be calculated by the equation $$\frac{(A_{ts1^\circ\lambda} - A_{tb1^\circ\lambda}) - (A_{ts2^\circ\lambda} - A_{tb2^\circ\lambda})}{(A_{t\,stand\,1^\circ\lambda} - A_{tb1^\circ\lambda}) - (A_{t\,stand\,2^\circ\lambda} - A_{tb2^\circ\lambda})} \times$$

$$\frac{\text{known calcium concentration}}{\text{of calcium standard}} = \frac{\text{concentration of calcium}}{\text{in the test sample.}}$$

Preferably, the primary wavelength is about 650 nm and the secondary wavelength is about 700 nm.

Table I (below) shows the effectiveness of bichromatic measurements in reducing spectral interferences from lipemia (turbidity) and hemolysis. Utilizing the above assay procedure, the following test samples were measured: a 12 mg % calcium sample, a 1,000 mg % triglycerides sample (INTRALIPID, obtainable from Kabi Vitrum, Inc., Alameda, Calif. 94501), and a 900 mg % hemoglobin sample. Assays were performed on these samples both with and without bichromatic measurements. When spectral measurements were made only at 650 nm, the error due to turbidity (INTRALIPID) was 34.2% (apparent calcium-arsenazo III formation), and the error due to hemolysis (hemoglobin) was 2.4% (apparent calcium-arsenazo III formation). However, when spectral measurements were also made at 700 nm and the absorbances at 700 nm subtracted from the absorbances at 650 nm (see equation above relating to bichromatic measurements), the error due to turbidity was only 5.5% and the error due to hemolysis was 0%.

TABLE I

| Absorbance | Without Bichromatic Measurements (650 nm) | Bichromatic Measurements (1° λ = 650 nm 2° λ = 700 nm) |
| --- | --- | --- |
| 12 mg % calcium | 0.801 Absorbance (A) | 0.792 A |
| 1000 mg % triglycerides (INTRALIPID) | 0.274 A | 0.044 A |
| 900 mg % hemoglobin | 0.002 A | 0.001 A |
| Error | | |
| INTRALIPID | 34.2% | 5.5% |
| 900 mg % hemoglobin | 2.4% | 0% |

The Hitachi family of automated analyzers is widely used. A member of that family, the Hitachi 717 automated analyzer, performs bichromatic measurements. The calcium reagent of the present invention may be divided into two reagents and utilized in performing a calcium assay on the Hitachi 717 by a. preparing a test blank by adding a sample of unknown calcium content to a first reagent that includes a buffer of sufficient type to provide a first reagent pH from about 8.5 to about 10, more preferably from about 8.5 to about 9.5 and most preferably from about 8.8 to about 9, and in sufficient concentration to maintain a pH, during the assay, within +/−0.1 pH units of the first reagent pH, at least one non-ionic surfactant, dimethylsulfoxide, and water;

b. preparing a test sample by adding the test blank to a second reagent that includes arsenazo III, dimethylsulfoxide, at least one non-ionic surfactant, 8-hydroxyquinoline, and water;

c. preparing a test standard blank by adding a standard of known calcium concentration to the first reagent;

d. preparing a test standard by adding the test standard blank to the second reagent;

e. spectrophotometrically measuring absorbances of the test sample, the test blank, the test standard, and the test standard blank at a primary wavelength (1°λ);

f. spectrophotometrically measuring absorbances of the test sample, the test blank, the test standard, and the test standard blank at a secondary wavelength (2°λ); and g. calculating the concentration of calcium in the test sample by the equation $$\frac{(A_{ts1^\circ\lambda} - A_{tb1^\circ\lambda}) - (A_{ts2^\circ\lambda} - A_{tb2^\circ\lambda})}{(A_{t\,stand\,1^\circ\lambda} - A_{t\,stand\,b1^\circ\lambda}) - (A_{t\,stand\,2^\circ\lambda} - A_{t\,stand\,b2^\circ\lambda})} \times$$

$$\frac{\text{known calcium concentration}}{\text{of calcium standard}} = \frac{\text{concentration of calcium}}{\text{in the test sample.}}$$

As specified in the Calcium Reagent discussion, inclusion of a non-ionic surfactant is not required, but is preferred, in the calcium reagent. Two non-ionic surfactants, such as BRIJ 35 (polyoxyethylene 23 lauryl ether) and TRITON X-100 (see Calcium Reagent Discussion), are most preferably included in the calcium reagent. Further, if a non-ionic surfactant is in the first reagent, it is preferable to include a non-ionic surfactant in the second reagent in order to keep turbidity clearing relatively constant during spectrophotometric measurements.

A specific formulation for reagents and a specific assay applicable to the Hitachi 717 automated bichromatic analyzer is described immediately below.

First Reagent (R1)

24 g AMPD, 2 ml of 30% (wt./vol. solution) BRIJ 35, 1.2 ml of TRITON X-100, and 100 ml of dimethylsulfoxide is added to 800 ml of deionized water. The resulting solution is mixed until homogeneous. The homogeneous solution is mixed with 10 g of CHELEX 100 for 30 minutes, then filtered to remove the CHELEX 100. The pH of the filtrate is adjusted to about 9 by the addition of concentrated hydrochloric acid. The pH 9 filtrate solution is then brought to about 1 liter volume by the addition of deionized water.

Second Reagent (R2)

800 mg of arsenazo III, 2 ml of 30% (wt./vol. solution) of BRIJ 35, 1.2 ml of TRITON X-100, and 4 g of 8-hydroxyquinoline is added to about 200 ml of dimethylsulfoxide. The resulting mixture is stirred until a homogeneous solution is obtained, and the volume of the homogeneous solution is brought to about 1 liter by the addition of deionized water.

On the Hitachi 717, a sample of unknown calcium content is added to the first reagent to form a test blank (tb). A test sample (ts) is prepared by adding the second reagent to the test blank. A test standard blank (t stand b) is prepared by adding a calcium standard of known calcium concentration to the first reagent. A test standard (t stand) is prepared by adding the test standard blank to the second reagent. For bichromatic correction, spectrophotometric measurements of the test blank, test sample, test standard blank, and test standard absorbances are performed at primary and secondary wavelengths (1°λ and 2°λ) as described above. Absorbances are compared and the concentration of calcium in the test sample is calculated by the equation $$\frac{(A_{ts1\cdot\lambda} - A_{tb1\cdot\lambda}) - (A_{ts2\cdot\lambda} - A_{tb2\cdot\lambda})}{(A_{t\,stand\,1\cdot\lambda} - A_{t\,stand\,b1\cdot\lambda}) - (A_{t\,stand\,2\cdot\lambda} - A_{t\,stand\,b2\cdot\lambda})} \times$$

$$\begin{array}{c} \text{known calcium} \\ \text{concentration of} = \\ \text{calcium standard} \end{array} \begin{array}{c} \text{concentration of} \\ \text{calcium in the} \\ \text{test sample.} \end{array}$$

Specifically, a person of ordinary skill in the art may perform a calcium assay on the Hitachi 717 using the above-stated reagents and the following exemplary chemistry parameters (analyzer settings):

| Hitachi 717 Chemistry Parameters | |
|---|---|
| Test | [CA] |
| Assay Code | [2]:[24]–[50] |
| Sample volume (μl) | [3] |
| R1 Volume (μl) | [250][100][0] |
| R2 Volume (μl) | [70][20][0] |
| Wavelength (nm) | [750][660] |
| Calib. Method | [1]-[0]-[0] |
| Std 1 Conc.-Pos | [0]-[1] |
| Std 2 Conc.-Pos | [*]-[2] |
| Std 3 Conc.-Pos | [0]-[0] |
| Std 4 Conc.-Pos | [0]-[0] |
| Std 5 Conc.-Pos | [0]-[0] |
| Std 6 Conc.-Pos | [0]-[0] |
| SD Limit | [0.1] |
| Duplicate Limit | [100] |
| Sensitivity Limit | [0] |
| Abs. Limit (Inc/Dec) | [0][0] |
| Prozone Limit | [0][0] |
| Expected Value (μmol/l) | [2.02]–[2.60] |
| Panic Value (μmol/l) | [*]-[*] |
| Instrument Factor | [1.0] |

*Denotes user specific settings.

A calcium assay as described above on the Hitachi 717 and performed analogously to the assay shown in Table I (analyzing 12 mg % calcium, INTRALIPID, and 900 mg % hemoglobin) resulted in less than 1% error due to INTRALIPID and no error due to hemoglobin.

The inventive reagent may also be utilized in an automated analyzer, such as the Hitachi 705, which performs test blank spectral measurements after rather than before test sample spectral measurements. In such a method, a test sample is formed by adding a sample of unknown calcium content to the single, stable calcium reagent (described under the Calcium Reagent section). The test blank is formed by adding the test sample to a calcium complexing reagent. A test standard and test standard blank are analogously formed by first adding a calcium standard of known calcium concentration to the single, stable calcium reagent (forming the test standard), then adding the calcium complexing reagent (forming the test standard blank).

The calcium complexing reagent complexes calcium, thereby disrupting the calcium-arsenazo III complex. The complexing reagent includes a complexing substance, a known antimicrobial agent, such as sodium azide, and deionized water. The complexing substance may be ethylenediamine tetraacetic acid (EDTA). However, EDTA salts, such as the disodium, tetrasodium, dipotassium and tetrapotassium salts of EDTA are preferred to the free acid form because they are more soluble in water.

A suitable calcium complexing reagent may be about 0.3 millimolar (mM) in EDTA and about 8 mM in sodium azide. More EDTA may be used. However, care must be taken to avoid using too much EDTA in automated analyzers that wash and reuse reaction vessels/cuvettes because EDTA may be difficult to wash out of the vessel/cuvette and its presence may adversely affect assays of some analytes.

Specifically, a person of ordinary skill in the art may perform a calcium assay on the Hitachi 705 using the following exemplary chemistry parameters:

| Chemistry Parameters for the Hitachi 705 | |
|---|---|
| Test | :CA |
| Assay Code | :Endpoint |
| Sample Volume (μl) | :3 |
| R1 Volume (μl) | :350 |
| R2 Volume (μl) | :50 |
| R3 Volume | : |
| Wavelength 1 | :700 nm |
| Wavelength 2 | :660 nm |
| Rgt. Blk. Abs. | :— |
| Rgt. Blk. Conc. | :0 |
| Std. Conc. | :*—*—* |
| Factor | :— |
| Std. Abs. Allowance | :10% |
| Normal Range L (μmol/l) | :2.02 |
| Normal Range H (μmol/l) | :2.60 |
| Abs. Limit (Rate) | : |
| Control I.D. No. | :*—*—* |

*Denotes user specific settings.
—Determined by Instrument.

In the above-stated parameters for the Hitachi 705, R1 is the specific calcium reagent described in the Calcium Reagent section. R2 is the calcium complexing reagent, which is an aqueous solution that is about 0.3 mM in EDTA, tetrasodium salt and 8 mM in sodium azide. The Hitachi 705 will perform bichromatic spectral measurements (absorbances) of the test sample, test blank, test standard and test standard blank. The calcium concentration of the test sample is then calculated by the equation shown above for the calcium assay performed on the Hitachi 717.

The principle of operation of an analyzer like the Hitachi 705, which performs spectral measurement of the test blank after spectral measurement of the test sample, is that spectral absorbance of the test sample is due to arsenazo III-calcium complex and any other chromatic substances which may be in the test sample. Addition of the calcium complexing reagent destroys color due to the arsenazo III-calcium complex and permits subtraction of color due to the other chromatic substances in the test sample.

Many changes could be made in the above procedures and many apparently widely different embodiments of this invention could be made without departing from the scope thereof, and it is intended that all matter contained in the above description shall be interpreted as illustrative and not in a limiting sense.

I claim:
1. A reagent for the assay of calcium, comprising:
   a. arsenazo III in sufficient amount to react with all calcium in a sample of unknown calcium content;
   b. 8-hydroxyquinoline in sufficient amount to bind all magnesium in the sample of unknown calcium content;
   c. a buffer that does not bind calcium competitively with arsenazo III and that provides a reagent pH from about 8.5 to about 10, the buffer being in sufficient amount to maintain pH within +/−0.1 pH units of the reagent pH when the reagent is added to the sample of unknown calcium content;

d. dimethylsulfoxide in sufficient amount to solubilize the 8-hydroxyquinoline in the reagent; and
e. water.

2. The reagent of claim 1, further comprising:
f. at least one non-ionic surfactant in sufficient amount to minimize lipid turbidity.

3. The reagent of claim 1, further comprising:
f. a first non-ionic surfactant; and
g. a second non-ionic surfactant, the combined concentration of the first and second non-ionic surfactants being sufficient to minimize lipid turbidity and to provide mutual solubility of the first and second non-ionic surfactants in the reagent.

4. The reagent of claim 1, wherein the buffer is such as to provide a reagent pH from about 8.5 to about 9.5.

5. The reagent of claim 1, wherein the buffer is such as to provide a reagent pH from about 8.8 to about 9.

6. A reagent for the assay of calcium, the reagent per liter comprising:
a. about 80 mg arsenazo III;
b. about ½ g 8-hydroxyquinoline;
c. about 21 g 2-amino-2-methyl-1,3-propandiol;
d. hydrochloric acid in sufficient amount to achieve a reagent pH of about 9;
e. about 100 ml dimethylsulfoxide;
f. about 2 ml polyoxyethylene 23 lauryl ether;
g. about 1.2 ml polyethylene glycol p-isooctylphenyl ether; and
h. water in sufficient amount to achieve a reagent volume of about 1 liter.

7. A method for the assay of calcium, comprising the steps of:
a. preparing a test sample (ts) by adding a sample of unknown calcium content to the reagent of claim 1;
b. preparing a test blank (tb) by adding deionized water to the reagent of claim 1;
c. preparing a test standard (t stand) by adding a calcium standard of known calcium concentration to the reagent of claim 1;
d. spectrophotometrically measuring absorbances (A) of the test sample, the test blank, and the test standard at a wavelength from about 600 nm to about 670 nm; and
e. calculating the concentration of calcium in the test sample by the equation $$\frac{A_{ts} - A_{tb}}{A_{t\,stand} - A_{tb}} \times \begin{array}{l}\text{known calcium}\\ \text{concentration of}\\ \text{calcium standard}\end{array} = \begin{array}{l}\text{concentration of}\\ \text{calcium in the}\\ \text{test sample.}\end{array}$$

8. A method for the assay of calcium, comprising the steps of:
a. preparing a test sample (ts) by adding a sample of unknown calcium content to the reagent of claim 2;
b. preparing a test blank (tb) by adding deionized water to the reagent of claim 2;
c. preparing a test standard (t stand) by adding a calcium standard of known calcium concentration to the reagent of claim 2;
d. spectrophotometrically measuring absorbances (A) of the test sample, the test blank, and the test standard at a wavelength from about 600 nm to about 670 nm; and
e. calculating the concentration of calcium in the test sample by the equation $$\frac{A_{ts} - A_{tb}}{A_{t\,stand} - A_{tb}} \times \begin{array}{l}\text{known calcium}\\ \text{concentration of}\\ \text{calcium standard}\end{array} = \begin{array}{l}\text{concentration of}\\ \text{calcium in the}\\ \text{test sample.}\end{array}$$

9. A method for the assay of calcium, comprising the steps of:
a. preparing a test sample (ts) by adding a sample of unknown calcium content to the reagent of claim 3;
b. preparing a test blank (tb) by adding deionized water to the reagent of claim 3;
c. preparing a test standard (t stand) by adding a calcium standard of known calcium concentration to the reagent of claim 3;
d. spectrophotometrically measuring absorbances (A) of the test sample, the test blank, and the test standard at a wavelength from about 600 nm to about 670 nm; and
e. calculating the concentration of calcium in the test sample by the equation $$\frac{A_{ts} - A_{tb}}{A_{t\,stand} - A_{tb}} \times \begin{array}{l}\text{known calcium}\\ \text{concentration of}\\ \text{calcium standard}\end{array} = \begin{array}{l}\text{concentration of}\\ \text{calcium in the}\\ \text{test sample.}\end{array}$$

10. The method of claim 7, wherein the test sample, the test blank, and the test standard are spectrophotometrically measured at a wavelength from about 650 nm to about 660 nm.

11. The method of claim 8, wherein the test sample, the test blank, and the test standard are spectrophotometrically measured at a wavelength from about 650 nm to about 660 nm.

12. A method for the assay of calcium, comprising the steps of:
a. preparing a test sample (ts) by adding a sample of unknown calcium content to the reagent of claim 6;
b. preparing a test blank (tb) by adding deionized water to the reagent of claim 6;
c. preparing a test standard (t stand) by adding a calcium standard of known calcium concentration to the reagent of claim 6;
d. spectrophotometrically measuring absorbances (A) of the test sample, the test blank, and the test standard at a wavelength from about 650 nm to about 660 nm; and
e. calculating the concentration of calcium in the test sample by the equation $$\frac{A_{ts} - A_{tb}}{A_{t\,stand} - A_{tb}} \times \begin{array}{l}\text{known calcium}\\ \text{concentration of}\\ \text{calcium standard}\end{array} = \begin{array}{l}\text{concentration of}\\ \text{calcium in the}\\ \text{test sample.}\end{array}$$

13. A method for the assay of calcium, comprising the steps of
a. preparing a test sample (ts) by adding a sample of unknown calcium content to the reagent of claim 1;
b. preparing a test blank (tb) by adding deionized water to the reagent of claim 1;
c. preparing a test standard (t stand) by adding a calcium standard of known calcium concentration to the reagent of claim 1;
d. spectrophotometrically measuring absorbances (A) of the test sample, the test blank, and the test standard at a primary wavelength (1°λ);

e. spectrophotometrically measuring absorbances (A) of the test sample, the test blank, and the test standard at a secondary wavelength ($2°\lambda$); and f. calculating the concentration of calcium in the test sample by the equation $$\frac{(A_{ts1°\lambda} - A_{tb1°\lambda}) - (A_{ts2°\lambda} - A_{tb2°\lambda})}{(A_{t\,stand\,1°\lambda} - A_{tb1°\lambda}) - (A_{t\,stand\,2°\lambda} - A_{tb2°\lambda})} \times$$

$$\frac{\text{known calcium concentration}}{\text{of calcium standard}} = \frac{\text{concentration of calcium}}{\text{in the test sample.}}$$

14. A method for the assay of calcium, comprising the steps of
   a. preparing a test sample (ts) by adding a sample of unknown calcium content to the reagent of claim 2;
   b. preparing a test blank (tb) by adding deionized water to the reagent of claim 2;
   c. preparing a test standard (t stand) by adding a calcium standard of known calcium concentration to the reagent of claim 2;
   d. spectrophotometrically measuring absorbances (A) of the test sample, the test blank, and the test standard at a primary wavelength ($1°\lambda$);
   e. spectrophotometrically measuring absorbances (A) of the test sample, the test blank, and the test standard at a secondary wavelength ($2°\lambda$); and
   f. calculating the concentration of calcium in the test sample by the equation $$\frac{(A_{ts1°\lambda} - A_{tb1°\lambda}) - (A_{ts2°\lambda} - A_{tb2°\lambda})}{(A_{t\,stand\,1°\lambda} - A_{tb1°\lambda}) - (A_{t\,stand\,2°\lambda} - A_{tb2°\lambda})} \times$$

$$\frac{\text{known calcium concentration}}{\text{of calcium standard}} = \frac{\text{concentration of calcium}}{\text{in the test sample.}}$$

15. A method for the assay of calcium, comprising the steps of
   a. preparing a test sample (ts) by adding a sample of unknown calcium content to the reagent of claim 3;
   b. preparing a test blank (tb) by adding deionized water to the reagent of claim 3;
   c. preparing a test standard (t stand) by adding a calcium standard of known calcium concentration to the reagent of claim 3;
   d. spectrophotometrically measuring absorbances (A) of the test sample, the test blank, and the test standard at a primary wavelength ($1°\lambda$);
   e. spectrophotometrically measuring absorbances (A) of the test sample, the test blank, and the test standard at a secondary wavelength ($2°\lambda$); and
   f. calculating the concentration of calcium in the test sample by the equation $$\frac{(A_{ts1°\lambda} - A_{tb1°\lambda}) - (A_{ts2°\lambda} - A_{tb2°\lambda})}{(A_{t\,stand\,1°\lambda} - A_{tb1°\lambda}) - (A_{t\,stand\,2°\lambda} - A_{tb2°\lambda})} \times$$

$$\frac{\text{known calcium concentration}}{\text{of calcium standard}} = \frac{\text{concentration of calcium}}{\text{in the test sample.}}$$

16. A method for the assay of calcium, comprising the steps of
   a. preparing a test sample (ts) by adding a sample of unknown calcium content to the reagent of claim 6;
   b. preparing a test blank (tb) by adding deionized water to the reagent of claim 6;
   c. preparing a test standard (t stand) by adding a calcium standard of known calcium concentration to the reagent of claim 6;
   d. spectrophotometrically measuring absorbances (A) of the test sample, the test blank, and the test standard at a primary wavelength ($1°\lambda$);
   e. spectrophotometrically measuring absorbances (A) of the test sample, the test blank, and the test standard at a secondary wavelength ($2°\lambda$); and
   f. calculating the concentration of calcium in the test sample by the equation $$\frac{(A_{ts1°\lambda} - A_{tb1°\lambda}) - (A_{ts2°\lambda} - A_{tb2°\lambda})}{(A_{t\,stand\,1°\lambda} - A_{tb1°\lambda}) - (A_{t\,stand\,2°\lambda} - A_{tb2°\lambda})} \times$$

$$\frac{\text{known calcium concentration}}{\text{of calcium standard}} = \frac{\text{concentration of calcium}}{\text{in the test sample.}}$$

17. A method for the assay of calcium comprising the steps of:
   a. preparing a test blank (tb) by adding a sample of unknown calcium content to a first reagent that includes a buffer that does not bind calcium competitively with arsenazo III and that provides a first reagent pH from about 8.5 to about 10, the buffer being in sufficient amount to maintain pH within $+/-0.1$ pH units of the first reagent pH when the first reagent is added to the sample of unknown calcium content, dimethylsulfoxide, and water;
   b. preparing a test sample (ts) by adding the test blank to a second reagent that includes arsenazo III, dimethylsulfoxide, 8-hydroxyquinoline, and water;
   c. preparing a test standard blank (t stand b) by adding a standard of known calcium concentration to the first reagent;
   d. preparing a test standard (t stand) by adding the test standard blank to the second reagent;
   e. spectrophotometrically measuring absorbances (A) of the test sample, the test blank, the test standard, and the test standard blank at a primary wavelength ($1°\lambda$);
   f. spectrophotometrically measuring absorbances (A) of the test sample, the test blank, the test standard, and the test standard blank at a secondary wavelength ($2°\lambda$); and
   g. calculating the concentration of calcium in the test sample by the equation $$\frac{(A_{ts1°\lambda} - A_{tb1°\lambda}) - (A_{ts2°\lambda} - A_{tb2°\lambda})}{(A_{t\,stand\,1°\lambda} - A_{t\,stand\,b1°\lambda}) - (A_{t\,stand\,2°\lambda} - A_{t\,stand\,b2°\lambda})} \times$$

$$\frac{\text{known calcium concentration}}{\text{of calcium standard}} = \frac{\text{concentration of calcium}}{\text{in the test sample.}}$$

18. A method for the assay of calcium comprising the steps of:
   a. preparing a test blank (tb) by adding a sample of unknown calcium content to a first reagent that includes a buffer that does not bind calcium competitively with arsenazo III and that provides a first reagent pH from about 8.5 to about 10, the buffer being in sufficient amount to maintain pH within $+/-0.1$ pH units of the first reagent pH when the first reagent is added to the sample of unknown calcium content, at least one non-ionic surfactant, dimethylsulfoxide, and water;
   b. preparing a test sample (ts) by adding the test blank to a second reagent that includes arsenazo III, dimethylsulfoxide, at least one non-ionic surfactant, 8-hydroxyquinoline, and water;
   c. preparing a test standard blank (t stand b) by adding a standard of known calcium concentration to the first reagent;

d. preparing a test standard (t stand) by adding the test standard blank to the second reagent;
e. spectrophotometrically measuring absorbances (A) of the test sample, the test blank, the test standard, and the test standard blank at a primary wavelength (1°λ);
f. spectrophotometrically measuring absorbances (A) of the test sample, the test blank, the test standard, and the test standard blank at a secondary wavelength (2°λ); and
g. calculating the concentration of calcium in the test sample by the equation $$\frac{(A_{ts1\cdot\lambda} - A_{tb1\cdot\lambda}) - (A_{ts2\cdot\lambda} - A_{tb2\cdot\lambda})}{(A_{t\,stand\,1\cdot\lambda} - A_{t\,stand\,b1\cdot\lambda}) - (A_{t\,stand\,2\cdot\lambda} - A_{t\,stand\,b2\cdot\lambda})} \times$$

$$\frac{\text{known calcium concentration}}{\text{of calcium standard}} = \frac{\text{concentration of calcium}}{\text{in the test sample.}}$$

19. A method for the assay of calcium, comprising the steps of:
   a. preparing a test sample (ts) by adding a first portion of a serum sample of unknown calcium content to the reagent of claim 1;
   b. preparing a serum blank (sb) by adding a second portion of the serum sample to saline;
   c. preparing a test blank (tb) by adding deionized water to the reagent of claim 1;
   d. preparing a test standard (t stand) by adding a calcium standard of known calcium concentration to the reagent of claim 1;
   e. preparing a test standard blank (t stand b) by adding the calcium standard to saline;
   f. spectrophotometrically measuring absorbances (A) of the test sample, the test blank, the serum blank, the test standard, and the test standard blank at a wavelength from about 600 nm to about 670 nm; and
   g. calculating the concentration of calcium in the test sample by the equation $$\frac{A_{ts} - (A_{tb} + A_{sb})}{A_{t\,stand} - (A_{tb} + A_{t\,stand\,b})} \times \begin{array}{l}\text{Known calcium}\\ \text{concentration of} =\\ \text{calcium standard}\end{array}$$

concentration of calcium in the test sample.

20. A method for the assay of calcium, comprising the steps of:
   a. preparing a test sample (ts) by adding a first portion of a serum sample of unknown calcium content to the reagent of claim 2;
   b. preparing a serum blank (sb) by adding a second portion of the serum sample to saline;
   c. preparing a test blank (tb) by adding deionized water to the reagent of claim 2;
   d. preparing a test standard (t stand) by adding a calcium standard of known calcium concentration to the reagent of claim 2;
   e. preparing a test standard blank (t stand b) by adding the calcium standard to saline;
   f. spectrophotometrically measuring absorbances (A) of the test sample, the test blank, the serum blank, the test standard, and the test standard blank at a wavelength from about 600 nm to about 670 nm; and
   g. calculating the concentration of calcium in the test sample by the equation $$\frac{A_{ts} - (A_{tb} + A_{sb})}{A_{t\,stand} - (A_{tb} + A_{t\,stand\,b})} \times \begin{array}{l}\text{known calcium}\\ \text{concentration of} =\\ \text{calcium standard}\end{array}$$

concentration of calcium in the test sample.

21. A method for the assay of calcium, comprising the steps of:
   a. preparing a test sample (ts) by adding a first portion of a serum sample of unknown calcium content to the reagent of claim 3;
   b. preparing a serum blank (sb) by adding a second portion of the serum sample to saline;
   c. preparing a test blank (tb) by adding deionized water to the reagent of claim 3;
   d. preparing a test standard (t stand) by adding a calcium standard of known calcium concentration to the reagent of claim 3;
   e. preparing a test standard blank (t stand b) by adding the calcium standard to saline;
   f. spectrophotometrically measuring absorbances (A) of the test sample, the test blank, the serum blank, the test standard, and the test standard blank at a wavelength from about 600 nm to about 670 nm; and
   g. calculating the concentration of calcium in the test sample by the equation $$\frac{A_{ts} - (A_{tb} + A_{sb})}{A_{t\,stand} - (A_{tb} + A_{t\,stand\,b})} \times \begin{array}{l}\text{known calcium}\\ \text{concentration of} =\\ \text{calcium standard}\end{array}$$

concentration of calcium in the test sample.

22. The method of claim 19, wherein the test sample, the test blank, the serum blank, the test standard, and the test standard blank are spectrophotometrically measured at a wavelength from about 650 nm to about 660 nm.

23. The method of claim 20, wherein the test sample, the test blank, the serum blank, the test standard, and the test standard blank are spectrophotometrically measured at a wavelength from about 650 nm to about 660 nm.

24. A method for the assay of calcium, comprising the steps of:
   a. preparing a test sample (ts) by adding a first portion of a serum sample of unknown calcium content to the reagent of claim 6;
   b. preparing a serum blank (sb) by adding a second portion of the serum sample to saline;
   c. preparing a test blank (tb) by adding deionized water to the reagent of claim 6;
   d. preparing a test standard (t stand) by adding a calcium standard of known calcium concentration to the reagent of claim 6;
   e. preparing a test standard blank (t stand b) by adding the calcium standard to saline;
   f. spectrophotometrically measuring absorbances (A) of the test sample, the test blank, the serum blank, the test standard, and the test standard blank at a wavelength from about 650 nm to about 660 nm; and g. calculating the concentration of calcium in the test sample by the equation $$\frac{A_{ts} - (A_{tb} + A_{sb})}{A_{t\,stand} - (A_{tb} + A_{t\,stand\,b})} \times \begin{array}{l}\text{known calcium}\\\text{concentration of}\\\text{calcium standard}\end{array} = \begin{array}{l}\text{concentration of}\\\text{calcium in the}\\\text{test sample.}\end{array}$$

25. A method for the assay of calcium comprising the steps of:
   a. preparing a test sample (ts) by adding a sample of unknown calcium content to the calcium reagent of claim 1;
   b. preparing a test blank (tb) by adding a calcium complexing reagent to the test sample, the calcium complexing reagent being an aqueous solution comprised of a complexing substance that disrupts the arsenazo III-calcium complex and an antimicrobial agent;
   c. preparing a test standard (t stand) by adding a standard of known calcium concentration to the calcium reagent of claim 1;
   d. preparing a test standard blank (t stand b) by adding the calcium complexing reagent to the test standard;
   e. spectrophotometrically measuring absorbances (A) of the test sample, the test blank, the test standard, and the test standard blank at primary and secondary wavelengths (1°λ and 2°λ); and
   f. calculating the concentration of calcium in the test sample by the equation $$\frac{(A_{ts1^\circ\lambda} - A_{tb1^\circ\lambda}) - (A_{ts2^\circ\lambda} - A_{tb2^\circ\lambda})}{(A_{t\,stand\,1^\circ\lambda} - A_{t\,stand\,b1^\circ\lambda}) - (A_{t\,stand\,2^\circ\lambda} - A_{t\,stand\,b2^\circ\lambda})} \times$$

$$\frac{\text{known calcium concentration}}{\text{of calcium standard}} = \frac{\text{concentration of calcium}}{\text{in the test sample.}}$$

26. A method for the assay of calcium comprising the steps of:
   a. preparing a test sample (ts) by adding a sample of unknown calcium content to the calcium reagent of claim 2;
   b. preparing a test blank (tb) by adding a calcium complexing reagent to the test sample, the calcium complexing reagent being an aqueous solution comprised of a complexing substance that disrupts the arsenazo III-calcium complex and an antimicrobial agent;
   c. preparing a test standard (t stand) by adding a standard of known calcium concentration to the calcium reagent of claim 2;
   d. preparing a test standard blank (t stand b) by adding the calcium complexing reagent to the test standard;
   e. spectrophotometrically measuring absorbances (A) of the test sample, the test blank, the test standard, and the test standard blank at primary and secondary wavelengths (1°λ and 2°λ); and
   f. calculating the concentration of calcium in the test sample by the equation $$\frac{(A_{ts1^\circ\lambda} - A_{tb1^\circ\lambda}) - (A_{ts2^\circ\lambda} - A_{tb2^\circ\lambda})}{(A_{t\,stand\,1^\circ\lambda} - A_{t\,stand\,b1^\circ\lambda}) - (A_{t\,stand\,2^\circ\lambda} - A_{t\,stand\,b2^\circ\lambda})} \times$$

$$\frac{\text{known calcium concentration}}{\text{of calcium standard}} = \frac{\text{concentration of calcium}}{\text{in the test sample.}}$$

27. A method for the assay of calcium comprising the steps of:
   a. preparing a test sample (ts) by adding a sample of unknown calcium content to the calcium reagent of claim 3;
   b. preparing a test blank (tb) by adding a calcium complexing reagent to the test sample, the calcium complexing reagent being an aqueous solution comprised of a complexing substance that disrupts the arsenazo III-calcium complex and an antimicrobial agent;
   c. preparing a test standard (t stand) by adding a standard of known calcium concentration to the calcium reagent of claim 3;
   d. preparing a test standard blank (t stand b) by adding the calcium complexing reagent to the test standard;
   e. spectrophotometrically measuring absorbances (A) of the test sample, the test blank, the test standard, and the test standard blank at primary and secondary wavelengths (1°λ and 2°λ); and
   f. calculating the concentration of calcium in the test sample by the equation $$\frac{(A_{ts1^\circ\lambda} - A_{tb1^\circ\lambda}) - (A_{ts2^\circ\lambda} - A_{tb2^\circ\lambda})}{(A_{t\,stand\,1^\circ\lambda} - A_{t\,stand\,b1^\circ\lambda}) - (A_{t\,stand\,2^\circ\lambda} - A_{t\,stand\,b2^\circ\lambda})} \times$$

$$\frac{\text{known calcium concentration}}{\text{of calcium standard}} = \frac{\text{concentration of calcium}}{\text{in the test sample.}}$$

28. A method for the assay of calcium comprising the steps of:
   a. preparing a test sample (ts) by adding a sample of unknown calcium content to the calcium reagent of claim 6;
   b. preparing a test blank (tb) by adding a calcium complexing reagent to the test sample, the calcium complexing reagent being an aqueous solution comprised of a complexing substance that disrupts the arsenazo III-calcium complex and an antimicrobial agent;
   c. preparing a test standard (t stand) by adding a standard of known calcium concentration to the calcium reagent of claim 6;
   d. preparing a test standard blank (t stand b) by adding the calcium complexing reagent to the test standard;
   e. spectrophotometrically measuring absorbances (A) of the test sample, the test blank, the test standard, and the test standard blank at primary and secondary wavelengths (1°λ and 2°λ); and
   f. calculating the concentration of calcium in the test sample by the equation $$\frac{(A_{ts1^\circ\lambda} - A_{tb1^\circ\lambda}) - (A_{ts2^\circ\lambda} - A_{tb2^\circ\lambda})}{(A_{t\,stand\,1^\circ\lambda} - A_{t\,stand\,b1^\circ\lambda}) - (A_{t\,stand\,2^\circ\lambda} - A_{t\,stand\,b2^\circ\lambda})} \times$$

$$\frac{\text{known calcium concentration}}{\text{of calcium standard}} = \frac{\text{concentration of calcium}}{\text{in the test sample.}}$$

* * * * *